(12) United States Patent
Anderson et al.

(10) Patent No.: US 9,962,492 B2
(45) Date of Patent: May 8, 2018

(54) SYRINGE ASSEMBLY (71) Applicant: CONSORT MEDICAL PLC, Hempstead (GB)

(72) Inventors: Ian Anderson, Burwell (GB); Matt Ekman, Macclesfield (GB)

(73) Assignee: CONSORT MEDICAL PLC, Hempstead (GB)

( * ) Notice: Subject to any disclaimer, the term of this patent is extended or adjusted under 35 U.S.C. 154(b) by 1 day.

(21) Appl. No.: 14/380,334

(22) PCT Filed: Feb. 22, 2013

(86) PCT No.: PCT/GB2013/050438
§ 371 (c)(1),
(2) Date: Aug. 21, 2014

(87) PCT Pub. No.: WO2013/124669
PCT Pub. Date: Aug. 29, 2013

(65) Prior Publication Data
US 2015/0011975 A1   Jan. 8, 2015

(30) Foreign Application Priority Data

Feb. 22, 2012 (GB) .................................. 1203015.1

(51) Int. Cl.
*A61M 5/28* (2006.01)
*A61M 5/20* (2006.01)
(Continued)

(52) U.S. Cl.
CPC .......... *A61M 5/284* (2013.01); *A61M 5/2066* (2013.01); *A61M 5/286* (2013.01);
(Continued)

(58) Field of Classification Search
CPC ................ A61M 5/284; A61M 5/2066; A61M 5/31596; A61M 2005/31598;
(Continued)

(56) References Cited

U.S. PATENT DOCUMENTS 3,076,456 A * 2/1963 Hunt, Jr. ......................... 604/89
3,699,961 A * 10/1972 Szpur .............................. 604/89
(Continued)

FOREIGN PATENT DOCUMENTS

CN   1221351 A1   6/1999
EP   0112574 A1 * 12/1983 .............. A61M 5/28
(Continued)

OTHER PUBLICATIONS

Patent translate: translation of EP0112574, Aug. 5, 2015.*
(Continued)

*Primary Examiner* — Bradley J Osinski
*Assistant Examiner* — Nilay Shah
(74) *Attorney, Agent, or Firm* — Taft Stettinius & Hollister LLP; Ryan O. White (57) ABSTRACT A syringe assembly having a barrel for containing one or more medicaments and a stopper disposed in the barrel defining and separating a first volume and a second volume within the syringe assembly. The stopper includes a permanent seal fluidly sealing the stopper to the barrel about the entire perimeter of the stopper intermediate the first volume and second volume, and a channel bypassing the permanent seal, the channel having a first opening in fluid communication with the second volume and a second opening selectively sealed from the first volume by a resilient seal. The resilient seal is moveable between a sealing configuration and an open configuration to selectively seal the channel from the first volume and is moveable from the sealing configuration to the open configuration upon fluid pressure (Continued)

in the first volume or second volume exceeding a first pressure threshold.

30 Claims, 6 Drawing Sheets

(51) Int. Cl.
   *A61M 5/315*   (2006.01)
   *A61M 5/32*    (2006.01)
   *A61M 5/178*   (2006.01)

(52) U.S. Cl.
   CPC ....... *A61M 5/31596* (2013.01); *A61M 5/3294* (2013.01); *A61M 2005/1787* (2013.01); *A61M 2005/31598* (2013.01)

(58) Field of Classification Search
   CPC ...... A61M 2005/1787; A61M 5/16827; A61M 2005/2451; A61M 5/3294; A61M 5/14
   See application file for complete search history.

(56) References Cited

U.S. PATENT DOCUMENTS

| | | | |
|---|---|---|---|
| 3,914,419 A | | 10/1975 | Haeger et al. |
| 4,929,230 A | * | 5/1990 | Pfleger ............... 604/90 |
| 4,941,876 A | | 7/1990 | Meyer et al. |
| 5,078,691 A | * | 1/1992 | Hamacher ............... 604/191 |
| 5,713,857 A | * | 2/1998 | Grimard et al. ............ 604/82 |
| 6,387,078 B1 | * | 5/2002 | Gillespie, III ............ 604/181 |
| 2002/0042592 A1 | | 4/2002 | Wilmont et al. |
| 2004/0171984 A1 | | 9/2004 | Greenfield |
| 2005/0245880 A1 | | 11/2005 | Howlett et al. |
| 2008/0255521 A1 | | 10/2008 | Kubo et al. |

FOREIGN PATENT DOCUMENTS

| | | |
|---|---|---|
| EP | 0112574 A | 7/1984 |
| EP | 1213036 A1 | 12/2002 |
| FR | 2750051 A | 12/1997 |
| JP | 2011-509751 A | 3/2011 |
| WO | 94/09839 A | 5/1994 |
| WO | 97/41909 A1 | 11/1997 |

OTHER PUBLICATIONS

International Search Report and Written Opinion for PCT/GB2013/050438 dated May 2, 2013.

UK Search Report of priority application No. GB1203015.1 dated May 23, 2012.

The State Intellectual Property Office of People's Republic of China—First Office Action for Chinese Application No. 201380010440.9, dated Dec. 29, 2015.

* cited by examiner

SYRINGE ASSEMBLY

This application is a U.S. national stage application under 35 U.S.C. § 371 of PCT International Application Serial No. PCT/GB2013/050438 which has an international filing date of Feb. 22, 2013, designates the United States of America, and claims the benefit of GB Application No. 1203015.1, which was filed on Feb. 22, 2012. The disclosures of each of these prior applications are hereby expressly incorporated by reference in their entirety.

This invention relates to an improved syringe assembly, and, more particularly, relates to an improved syringe assembly having a stopper defining and separating a first volume and a second volume within the syringe assembly.

BACKGROUND

It is known in the prior art to provide a syringe assembly with a stopper that defines and separates a first volume and a second volume within the syringe assembly. Such arrangements are used in mixing devices where two or more medicaments or other substances are mixed prior to delivery to an injection site, or in devices where two or more medicaments or other substances are delivered to an injection site separately and sequentially.

US-A-2005/0245880 (Howlett et al.) describes a multi-chamber, sequential dose dispensing syringe that has a moveable valve assembly that has a mechanical impact sensor that causes the valve to open when the valve assembly impacts ("bottoms out") with the bottom internal end of the syringe barrel.

A two-compartment sequential dose device for sequentially delivering doses of multivitamin preparation is described in U.S. Pat. No. 3,914,419 (American Cyanamid Company). The two compartments are separated by a stopper that has a central valved passage for allowing multivitamin preparation in the upper chamber to pass out through the needle after delivery of the multivitamin preparation in the lower chamber adjacent the needle.

FR-A-2750051 (Debiotech SA) and U.S. Pat. No. 4,929,230 (Pfleger) each describe a medical syringe having a free piston slidable in the barrel of the syringe for fluidly separating two internal volumes in the syringe. The free piston maintains a sealing configuration until it bottoms out at the bottom internal end of the syringe barrel, at which point fluid from the lower volume has been delivered through the needle of the syringe under the force of an upper plunger in the barrel of the syringe. Fluid pressure in the upper volume then causes the whole free piston to deform to allow fluid from the upper volume to bypass the free piston and exit through the needle.

A similar device is described in US-A-2008/0255521 (Hisamitsu Pharmaceutical Co. Inc.) except formations at the bottom internal end of the syringe cause the free piston to deform allowing fluid in the upper volume to bypass the free piston and exit the syringe through the needle.

Another syringe for sequentially administering different fluids is described in US-A-2004/0171984 (Greenfield) which also has a floating piston which acts to selectively separate two fluid volumes in the syringe. In one described embodiment, the floating piston is made of a compressible body that has a central valve that opens upon axial compression of the body.

U.S. Pat. No. 5,713,857 (Becton Dickinson France, S.A.) describes a stopper for use in a sequential delivery device. The stopper has a collapsible portion down one side that collapses when a predetermined fluid pressure is exceeded such that an axial channel is opened up along the side of the stopper. Thus, in a collapsed configuration, the stopper no longer forms a complete circumferential seal with the inner surface of the syringe barrel to allow the passage of fluid.

An automatic injection device for mixing a dry medicament component and a fluid (such as a diluent) and subsequently delivering the mixture/solution is described in US-A-2002/042592 (Wilmot, John G. et al.). A floating stopper initially separates the dry component from the wet component and is moveable to a position where a fluid passageway is opened which fluidly connects the volumes containing the wet and dry components. The fluid passageway is described as recesses (acting as bypass channels) in the inner surface of the syringe barrel. In an alternative described embodiment, the inner surface of the syringe barrel comprises ribs that distort the stopper when it reaches a particular axial position within the barrel to allow fluid to bypass the stopper and mix with the dry component.

A further two-compartment syringe is described in EP-A-0112574 (Meditec S.A.) which has a floating stopper having a central valve assembly for selectively allowing fluid communication between the two volumes separated by the stopper. The central valve assembly consists of a blocking component moveable relative to the remainder of the stopper between a blocking position where the central valve assembly is closed and an open position where the central valve assembly is open and fluidly connects the two compartments. The blocking component is biased by a spring to the blocking position so that a force (such as fluid pressure) is required to move the blocking component to the open position.

An automatic injector device is described in WO-A-9409839 which has a plunger rod disposed in a syringe barrel with a flexible stopper at the end of the plunger rod. Initially, the flexible stopper separates a dry medicament component from a fluid in a compartment rear of the dry compartment. The plunger rod and flexible stopper are moved rearwardly into the fluid compartment to initiate mixing as the flexible element flexes during movement through the fluid allowing fluid to bypass the flexible element and mix with the dry component. To actuate delivery of the mixed medicament, a rigid stopper is moved forward through the barrel of the syringe to expel mixed medicament from the syringe through the needle.

It is an object of the present invention to provide an improved or alternative syringe assembly that permits the selective separation of volume spaces therein.

BRIEF SUMMARY OF THE DISCLOSURE

The present invention is defined in the appended claims.

In accordance with a first aspect of the present invention there is provided a syringe assembly comprising:
  a barrel for containing one or more medicaments, a narrowed outlet for allowing the expulsion of said one or more medicaments from said barrel through said outlet; and
  a stopper disposed in the barrel defining and separating a first volume and a second volume within the syringe assembly, the stopper comprising:
    a permanent seal fluidly sealing the stopper to the barrel about the entire perimeter of the stopper intermediate the first volume and second volume; and
    a channel bypassing the permanent seal, the channel having a first opening in fluid communication with the second volume and a second opening selectively sealed from the first volume by a resilient seal;

where the resilient seal is moveable between a sealing configuration and an open configuration to selectively seal the channel from the first volume, where in the sealing configuration the resilient seal fluidly seals the stopper to the barrel so as to fluidly isolate said second opening of the channel from the first volume, and in the open configuration the second opening of the channel is in fluid communication with the first volume; and wherein the resilient seal is moveable from the sealing configuration to the open configuration upon fluid pressure in the first volume or second volume exceeding a first pressure threshold.

Preferably, the stopper is axially moveable within the barrel upon application of an axial force on the stopper.

In one embodiment, the axial force required to move the stopper within the barrel is less than the force provided by a fluid at the first pressure threshold.

In an alternative embodiment, the axial force required to move the stopper within the barrel is greater than the force provided by a fluid at the first pressure threshold.

In any embodiment, the resilient seal may comprise one or more flexible elements, wherein said one or more flexible elements preferably partly extends circumferentially around said stopper and the remainder of the stopper forms a seal with the barrel circumferentially around said one or more flexible elements. Preferably, said one or more flexible elements extends entirely circumferentially around said stopper. The resilient seal preferably comprises at least two flexible elements, wherein the at least two flexible elements are preferably axially aligned with one another.

Preferably, the channel comprises at least one axial channel part and at least one additional channel part arranged substantially perpendicularly to said at least one axial channel and in fluid communication therewith.

In one preferable embodiment, the permanent seal comprises at least one flange projecting outwardly from said stopper about the entire perimeter of the stopper. The permanent seal may comprise at least two flanges projecting outwardly from said stopper about the entire perimeter of the stopper, wherein the at least two flanges are arranged in axial alignment with one another.

The syringe assembly optionally comprises a pressure source for pressurising a fluid in the barrel. Said pressure source may comprise an axially moveable plunger element disposed in the barrel, where the stopper is disposed in the barrel intermediate the plunger element and the narrowed outlet of the barrel. Preferably, said plunger element comprises a plunger stopper and a plunger rod connected to the plunger stopper for axially moving the plunger stopper in the barrel. Preferably, said pressure source includes a power source.

Preferably, one or both of said first volume and second volume is a medicament volume for containing one or more medicaments.

In one embodiment, said first volume is a first medicament volume for containing a first medicament and said second volume is a second medicament volume for containing a second medicament. Said first medicament volume may contain a first fluidic medicament and said second medicament volume contains a second fluidic medicament.

Said first volume may be a medicament volume for containing a medicament and said stopper is arranged in said barrel to selectively isolate the medicament volume from the outlet of the barrel, wherein preferably, said medicament volume contains a fluidic medicament.

In one embodiment, the stopper further comprises a friction clamp that is moveable between a clamping position and a non-clamping position, where a higher force is required to axially move the stopper in the barrel when the friction clamp is in the clamping position than when the friction clamp is in the non-clamping position. The syringe assembly preferably further comprises a moveable plunger element disposed in the barrel for pressurising a fluid in the first volume, where the stopper is disposed in the barrel intermediate the plunger element and the narrowed outlet of the barrel, wherein the plunger element comprises a key and the stopper comprises a socket complementary to said key, and wherein engagement of the key in the socket moves said friction clamp to said non-clamping position. Preferably, the stopper further comprises a nozzle or spray head at the first opening of the stopper.

Said first volume may contain a fluidic substance and said second volume contains a dry or lyophilized substance.

The syringe assembly may further comprise a needle in fluid communication with the narrowed outlet of said barrel.

Said barrel and said narrowed outlet may be integrally formed. That is, the narrowed outlet may be a hole in the delivery (forward) end of the syringe barrel, where the hole has a diameter less than the diameter of the barrel (as in a "standard" syringe).

Preferably said barrel tapers towards said narrowed outlet.

In one preferable embodiment, said stopper is a first stopper, and the syringe assembly further comprises one or more additional stoppers each comprising the features of the first stopper as defined in accordance with the first aspect of the present invention, wherein the one or more additional stoppers separate and define further volumes within the syringe assembly axially rearward of the first stopper.

In accordance with a second aspect of the present invention, there is provided an autoinjector comprising a syringe assembly according to the first aspect of the present invention.

In accordance with a third aspect of the present invention, there is provided a method of using a syringe assembly comprising the steps of:
i) providing a syringe assembly according to the first aspect of the present invention where the axial force required to move the stopper within the barrel is less than the force provided by a fluid at the first pressure threshold, the syringe assembly containing a fluid in the first volume; and
ii) applying a force to pressurise the fluid so that the resilient seal moves to the open configuration and permits the expulsion of the fluid through the narrowed outlet via the channel of the stopper.

In accordance with a fourth aspect of the present invention, there is provided a method of using a syringe assembly comprising the steps of:
i) providing a syringe assembly according to the first aspect of the present invention where the axial force required to move the stopper within the barrel is less than the force provided by a fluid at the first pressure threshold, the syringe assembly containing a first fluid in the first volume and a second fluid in the second volume;
ii) applying a force to pressurise the first fluid to move the stopper axially forwardly within the barrel to expel the second fluid through the narrowed outlet;
iii) allowing the stopper to travel axially forwardly in the barrel to its forwardmost position; and
iv) continuing to apply a force to pressurize the first fluid so that the resilient seal moves to the open configuration and permits the expulsion of the first fluid through the narrowed outlet via the channel of the stopper.

In one embodiment, the syringe assembly provided in step i) further comprises a first applicator in fluid communication with the narrowed outlet, wherein subsequent to performing step ii) and prior to performing step iv) the first applicator is replaced with a second applicator. Further preferably, one or both of the first applicator and second applicator is a needle.

In accordance with a fifth aspect of the present invention, there is provided a method of using a syringe assembly comprising the steps of:
  i) providing a syringe assembly according to the first aspect of the present invention where the axial force required to move the stopper within the barrel is greater than the force provided by a fluid at the first pressure threshold, the syringe assembly containing a fluidic substance in the first volume and a dry or lyophilized substance in the second volume;
  ii) applying a force to pressurise the fluidic substance so that the resilient seal moves to the open configuration and permits the flow of the fluidic substance from the first volume to the second volume via the channel to form a solution or mixture in the second volume; and
  iii) applying a force to the stopper to move the stopper axially forwardly so as to expel the solution or mixture from the second volume through the narrowed outlet.

Preferably, the applied forces are provided by moving a plunger element axially forwardly in the barrel, wherein the stopper is disposed intermediate the plunger element and the narrowed outlet, and wherein the force applied to the stopper in step iii) occurs when the plunger element contacts the stopper following the expulsion of substantially all of the fluidic substance from the first volume.

The stopper preferably further comprises a friction clamp that is moveable between a clamping position and a non-clamping position, where a higher force is required to axially move the stopper in the barrel when the friction clamp is in the clamping position than when the friction clamp is in the non-clamping position, wherein the plunger element comprises a key and the stopper comprises a socket complementary to said key, and wherein engagement of the key in the socket moves said friction clamp to said non-clamping position.

BRIEF DESCRIPTION OF THE DRAWINGS

Embodiments of the invention are further described hereinafter with reference to the accompanying drawings, in which.

DETAILED DESCRIPTION

Figure 1A:
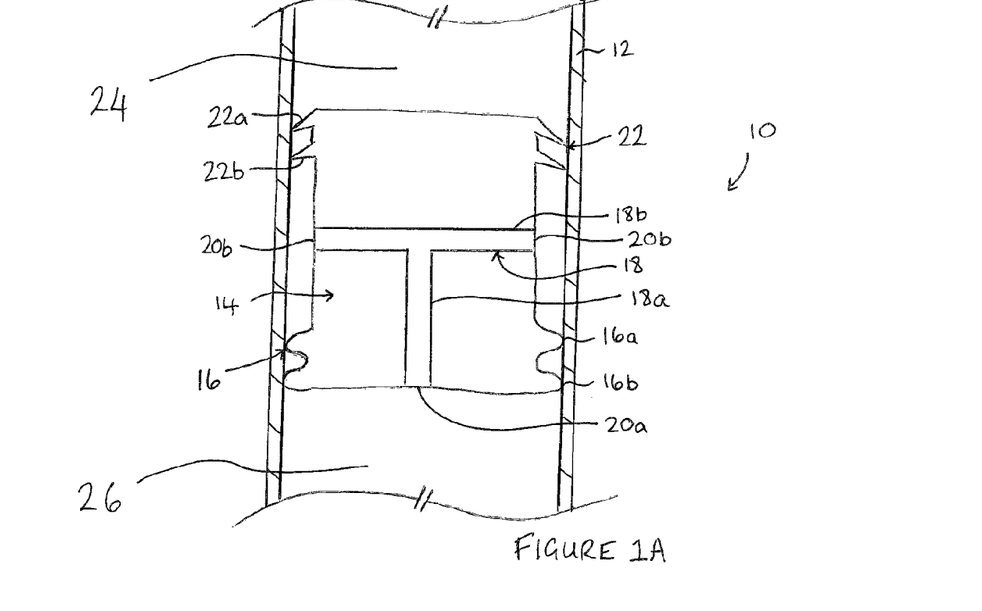
FIG. 1A is a partial cross sectional view of a syringe assembly in accordance with an embodiment of the present invention, comprising a stopper in a sealing configuration.
Figure 1B:
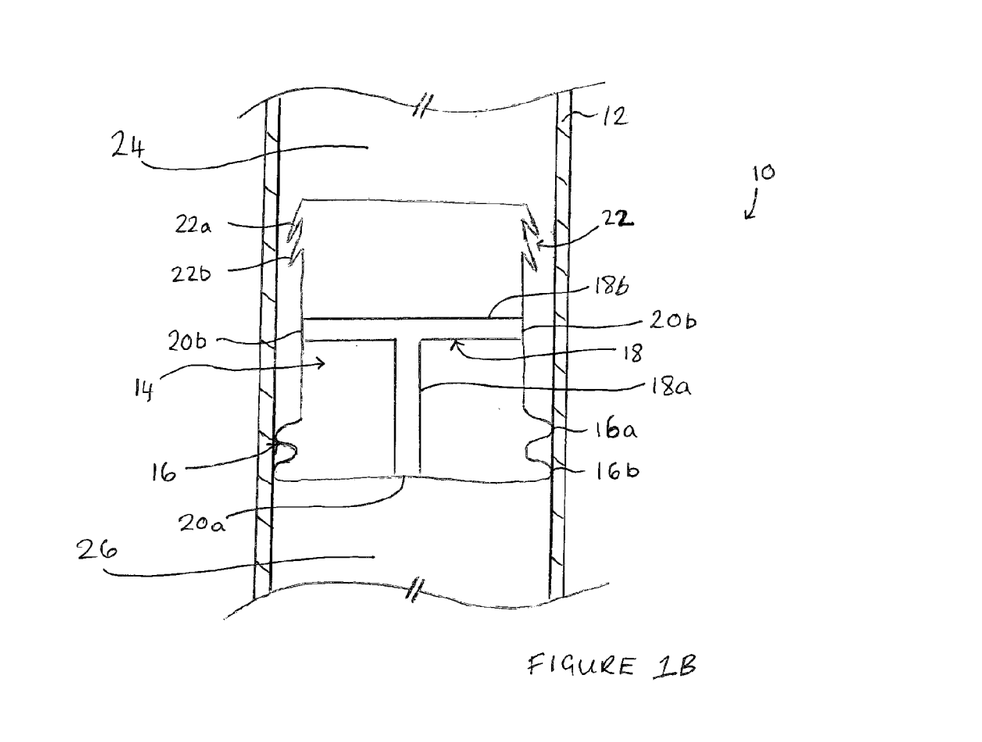
FIG. 1B is a partial cross sectional view of the syringe assembly of FIG. 1A where the stopper is in an open configuration.

FIGS. 1A and 1B each show a partial cross section of a syringe assembly 10 in accordance with an embodiment of the present invention in which a stopper 14 is disposed in a barrel 12 of the syringe assembly 10. The barrel 12 and stopper 14 are generally cylindrical in shape.

The skilled reader will appreciate that references to "axial" or "longitudinal" directions and axes (or similar) are considered to be parallel to the sides defining the barrel 12, with "radial" directions considered to be perpendicular to the longitudinal axis and extending outwards from a longitudinal axis running through the circular center of the syringe assembly 10. Similarly, "circumferential" directions are considered to be defined about a longitudinal axis running through the circular center of the syringe assembly 10.

References to "forward", "front", "lower", "below" or the like are considered to denote a direction or point at or towards a delivery end of the syringe assembly (i.e. the end that medicament is expelled from). Similarly, references to "rearward", "rear", "upper", "above" or the like are considered to denote a direction at or towards the end of the syringe assembly that is opposite the delivery end.

The stopper 14 has a permanent seal 16 formed by a pair of axially aligned flanges 16a, 16b extending radially from the stopper 14 and forming a fluid tight seal with the barrel 12 around the entire perimeter (circumference) of the stopper 14 at a forward end thereof. In alternative embodiments, any formation or configuration that is capable of forming a fluid-tight seal with the barrel 12 may form the permanent seal 16. Indeed, the present invention is not limited to having two such formations, and any number of flanges 16a, 16b or alternative formations or configurations may be used.

The stopper 14 has a resilient seal 22 axially rearward of the permanent seal 16 where the resilient seal 22 is formed of a pair of axially aligned flexible elements 22a, 22b that extend radially from the stopper 14 and extend around the entire circumference of the stopper 14. As is described in more detail below, the resilient seal 22 is moveable between a sealing configuration (as shown in FIG. 1A) and an open configuration (as shown in FIG. 1B), where in the sealing configuration, the resilient seal 22 fluidly seals the stopper 14 to the barrel 12, and in the open configuration, the resilient seal 22 does not fluidly seal the stopper 14 to the barrel 12.

The stopper 14 defines and separates a first volume 24 of the syringe assembly 10 and a second volume 26 of the syringe assembly 10 which are each capable of containing a medicament or other substance.

A channel 18 passes through the stopper 14 and has a first opening 20a in fluid communication with the first volume 26 and two second openings 20b that are each selectively sealed from the second volume 24 by the resilient seal 22. In the embodiment shown in FIGS. 1A and 1B, the channel 18 has a first axial channel part 18a and a second channel part 18b arranged substantially perpendicularly to the first axial channel part 18a. The first opening 20a is associated with the first axial channel part 18a and the two second openings 20b are associated with the second channel part 18b. In the specific embodiment depicted in FIGS. 1A and 1B, the channel 18 is T-shaped in cross-section.

When the resilient seal 22 is in the sealing configuration, the first volume 24 is fluidly isolated from the second volume 26 by the stopper 14. Conversely, when the resilient seal 22 is in the open configuration the first volume 24 is in fluid communication with the second volume 26 via the channel 18. Thus, since the resilient seal 22 is moveable between the sealing configuration and the open configuration, so too is the stopper 14 as a whole, since it selectively fluidly isolates and fluidly connects the first volume 24 and second volume 26 via the channel 18 depending on the configuration of the resilient seal 22.

The resilient seal 22 is moved from the sealing configuration to the open configuration when a force incident on the resilient seal 22 exceeds at predetermined threshold. Typically, such a force will arise when the fluid pressure of a fluid acting on the resilient seal 22 exceeds a predetermined threshold. For example, if the first volume was filled with a fluid (such as a fluidic medicament), then the resilient seal would move from the sealing configuration to the open configuration when the pressure of the fluid exceeded the predetermined threshold. When the pressure exceeds the predetermined threshold, the flexible elements 22a,22b of the resilient seal 22 flex or deflect so as to move away from the barrel 12 and open a fluid pathway allowing fluid to bypass the resilient seal 22. Alternative components may form the resilient seal 22 in place of the flexible elements 22a,22b that deform, deflect, flex or otherwise move to open a fluid pathway between the stopper 14 and the barrel 12 upon application of a predetermined force. In the embodiment shown in FIG. 1B, the flexible elements 22a,22b are shown to be flexed or deflected in a forward direction, such as one might expect to result from the pressure of a fluid in the first volume exceeding the predetermined threshold. However, the resilient seal 22 may be configured to be bi-directional such that a fluid in the second volume 26 is capable of causing the resilient seal 22 to move from the sealing configuration to the open configuration when the pressure of the fluid in the second volume 26 exceeds the predetermined pressure threshold.

In both sealing and open configurations, the permanent seal 16 remains in place and maintains a seal between the stopper 14 and the barrel 12 at the forward end of the stopper 14. Thus, a fluid connection is only formed between the first volume 24 and the second volume 26 when the resilient seal 22 is in the open configuration. Even when the resilient seal 22 is in the open configuration, fluid must flow along several axes in order to bypass the permanent seal 16 through the channel 18. This arrangement therefore provides a labyrinth pathway between the first volume 24 and the second volume 26, as opposed to a straight channel. A benefit of the labyrinth arrangement is that the likelihood of fluid flow from the first volume to the second volume is substantially reduced in the event that the resilient seal 22 is inadvertently moved to the open configuration for a short period of time. One advantage of having the resilient seal 22 acting between the stopper 14 and the barrel 12 is that this provides a low friction arrangement (particularly when the internal surface of the syringe barrel 12 is siliconised, which it often is) making the resilient seal 22 more reliable at opening when desired, since friction will have less influence of the predetermined pressure threshold.

Figure 2A:
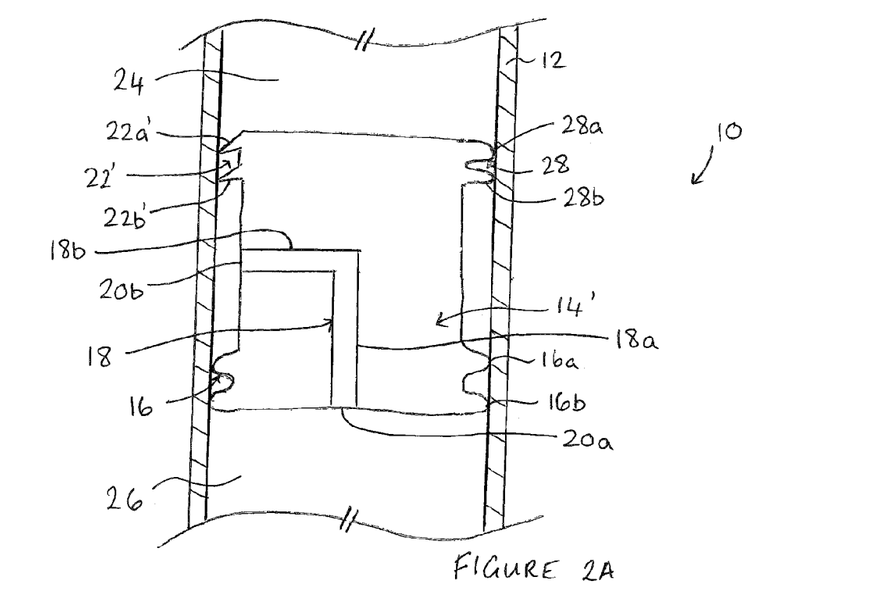
FIG. 2A is a partial cross sectional view of a syringe assembly in accordance with an alternative embodiment of the present invention, comprising a stopper in a sealing configuration.
Figure 2B:
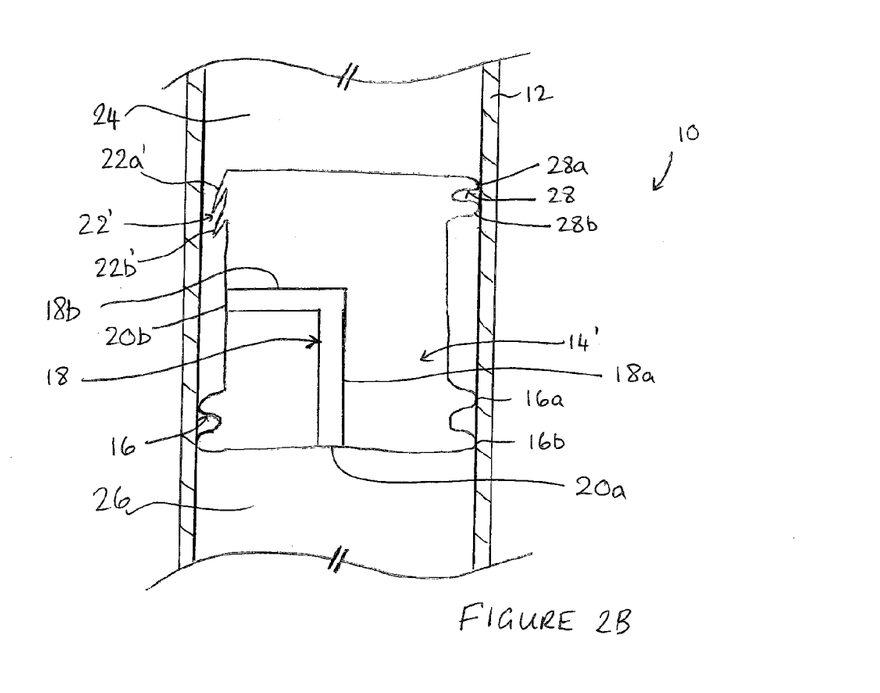
FIG. 2B is a partial cross sectional view of the syringe assembly of FIG. 2A where the stopper is in an open configuration.

An alternative embodiment of the invention is shown in FIGS. 2A and 2B in which the syringe assembly 10 comprises an alternative stopper 14'. Apart from the alternative stopper 14', the syringe assembly 10 is otherwise identical to that described above in relation to FIGS. 1A and 1B. The alternative stopper 14' has a permanent seal 16 identical to that described above in relation to FIGS. 1A and 1B, and comprises a resilient seal 22. The resilient seal 22 depicted in FIGS. 2A and 2B is formed of a pair of flexible elements 22a',22b' each extending radially from the stopper 14' and arranged in axial alignment with one another. However, different to the resilient seal 22 of FIGS. 1A and 1B, the resilient seal 22' of FIGS. 2A and 2B does not extend entirely circumferentially around the stopper 14' but is otherwise identical to resilient seal 22. Instead, the resilient seal 22' extends partly around the circumference of the stopper 14' and a second permanent seal 28 formed of a pair of flanges 28a,28b extending radially from the stopper 14' extend around the remainder of the circumference of the stopper 14' The second permanent seal 28 maintains a permanent seal between the stopper 14' and the barrel 12 across the extent of the circumference that it extends.

The stopper 14' has a channel 18 that bypasses the permanent seal 16 and is formed of a first axial channel part 18a and a second channel part 18b arranged substantially perpendicularly to the first axial channel part 18a. A first opening 20a is associated with the first axial channel part 18a and a single second opening 20b is associated with the second channel part 18b. The channel 18 of FIGS. 2A and 2B is L-shaped in cross section, in contrast to the channel 18 of FIGS. 1A and 1B which is T-shaped in cross section. However, either channel arrangement may be used in either embodiment. Alternatively, other channel arrangements may be employed that bypass the permanent seal 16 from an outer radial position via an inner radial position that is radially inwards of the permanent seal 16.

In preferable embodiments, the stopper 14,14' is made from a deformable elastomeric material that is able to achieve a fluid tight seal with the barrel 12.

The resilient seal 22' and the second permanent seal 28 are arranged relative to one another such that when the resilient seal 22' is in the sealing configuration (as shown in FIG. 2A) the combination of the resilient seal 22' and the second permanent seal 28 fluidly isolate the second opening 20b of the channel 18 from the first volume 24, and hence fluidly isolate the first volume 24 from the second volume 26. In the open configuration (as shown in FIG. 2B), the resilient seal 22' permits a fluid pathway that fluidly connects the first volume 24 to an annulus circumferentially surrounding the stopper 14' between the axial positions of the permanent seal 16 and the second permanent seal 28.

In an alternative embodiment, axial ribs or similar formations (not shown) may be arranged on the stopper 14' on either side of the second opening in each circumferential direction so as to form an axial channel that forms a circumferential boundary around the second opening and seals with the barrel 12. In this embodiment, the axial channel would be bound at a forward end by the permanent seal 16 and the axial channel would be bound at a rear end by resilient seal 22'. Since the second opening 20b is disposed within the bound axial channel, the second permanent seal 28 would not be necessary, however it is preferable that it still be present to minimise the risk of inadvertent fluid flow from the first volume 24 to the second volume 26.

Figure 3A:
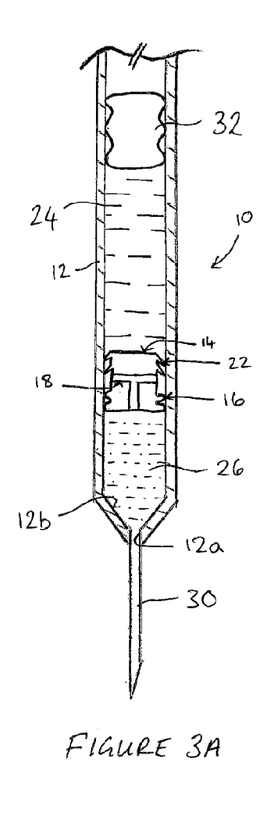
FIG. 3A is a partial cross sectional view of a syringe assembly in accordance with an embodiment of the present invention containing two fluids prior to actuation.
Figure 3B:
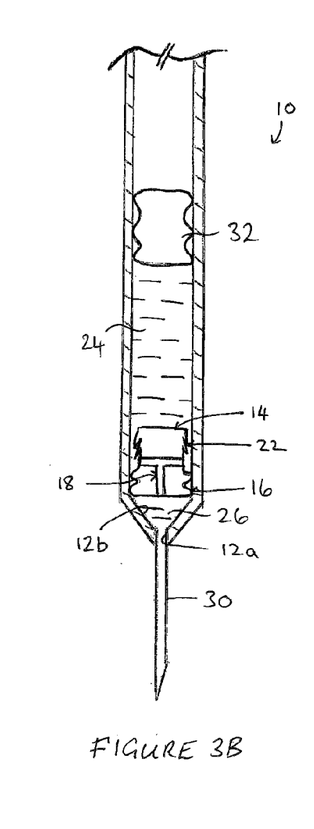
FIG. 3B is a partial cross sectional view of the syringe assembly of FIG. 3A during delivery.
Figure 3C:
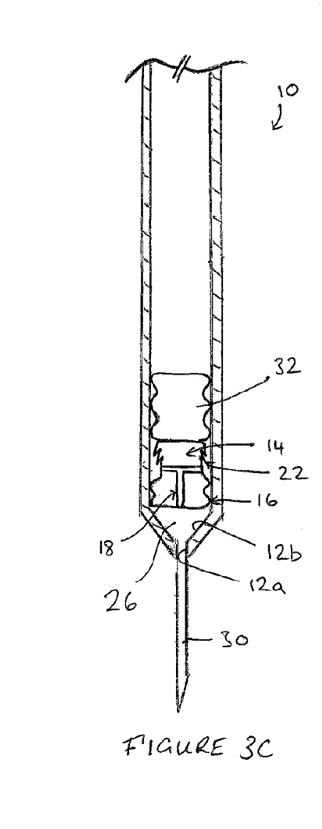
FIG. 3C is a partial cross sectional view of the syringe assembly of FIGS. 3A and 3B after delivery.

A preferred mode of operation and arrangement of the syringe assembly 10 is shown in FIGS. 3A to 3C. FIG. 3A shows the syringe assembly 10 prior to actuation containing a first fluid in the first volume 24 and a second fluid in the second volume 26. The first and second fluids may be medicaments and/or may be the same or different to one another. In the embodiment shown in FIG. 3A, the first volume 24 is greater than the second volume 26, however this need not necessarily be the case.

The barrel 12 has a tapered forward portion 12b that tapers to a narrowed opening or outlet 12a at the forwardmost end of the barrel 12, where the narrowed opening 12a has a diameter less than the diameter of the barrel 12. A hollow needle 30 is connected to the opening 12a of the barrel 12 to permit the expulsion of fluid from the barrel 12 through the opening 12a.

Rearward of the stopper 14 there is a plunger element 32 in the form of a plunger stopper disposed in the barrel 12. In the embodiment of FIGS. 3A to 3C, the first volume 24 is defined as the volume between the plunger element 32 and the stopper 14 and the second volume is defined as the volume in the syringe assembly 10 forward of the stopper 14 and may include the volume inside the hollow needle 30.

The stopper 14 is axially displaceable within the barrel 12 upon the application of an axial force on the stopper 14. Similarly, the plunger element 32 is axially displaceable within the barrel 12 upon the application of an axial force on the plunger element 32.

To actuate the syringe assembly 10, the needle 30 is inserted into an injection site and the plunger element is moved axially forwards within the barrel 12. The axially forward movement of the plunger element 32 may be achieved using a power source or by manually moving the plunger element 32. The plunger element 32 may additionally comprise a plunger rod connected to the plunger stopper to facilitate axial movement of the plunger stopper within the barrel 12. As the plunger element 32 moves axially forwards within the barrel 12, it increases the fluid pressure of the first fluid in the first volume 24. Due to the incompressible nature of the first fluid, the force from the plunger element 32 is transferred axially to the stopper 14. The skilled reader will appreciate that any suitable mechanism that can apply a force to the first fluid may be used in alternative embodiments in place of the plunger element 32.

The stopper 14 is configured such that the axial force required to axially move the stopper 14 within the barrel 12 is less than the force provided by a fluid at the pressure threshold that determines when the resilient seal 22 moves from the sealing configuration to the open configuration.

Therefore, initial forward force from the plunger element 32 on the first fluid causes the stopper 14 to move axially forwardly within the barrel 12. This action increases the pressure of the second fluid contained in the second volume 26 and causes the second fluid to be expelled from the syringe assembly 10 through the opening 12a and needle 30. Assuming that a continual axially forward force is applied on the plunger element 32, the stopper 14 will continue to move axially forwards and expel the second fluid until the stopper 14 reaches the tapered forward portion 12b of the barrel 12. At this point, the axially forward force acting on the stopper 14 is met with an equal and opposite (i.e. axially rearward) reaction force from the tapered forward portion 12b of the barrel 12 and the stopper 14 ceases to move forwards. Subsequent force on the plunger element 32 causes the pressure of the first fluid in the first volume 24 to increase in pressure until the predetermined pressure threshold required to move the resilient seal 22 from the sealing configuration to the open configuration is exceeded. Once exceeded, the resilient seal 22 moves from the sealing configuration to the open configuration and the first fluid in the first volume 24 bypasses the permanent seal 18 into the second volume 26 and is expelled out of the syringe assembly through the opening 12a and the needle 30, as shown in FIG. 3B.

Further force on the plunger element 32 causes the plunger element 32 to move further axially forwards towards the now stationary stopper 14, decreasing the first volume 24 as it does so. Eventually, the plunger element 32 reaches the stopper 14 and reduces the first volume 24 to substantially zero, as shown in FIG. 3C. At this point, two volumes of fluid have been expelled from the syringe assembly 10 and delivery is complete. The needle 30 may then be removed from the injection site.

The device described in relation to FIGS. 3A to 3C may thus be used to deliver two sequential doses of medicament to an injection site, where the stopper 14 ensures the two volumes of fluid remain separate from one another prior to actuation. A syringe assembly 10 of this type may be useful for delivery of two medicaments that are unstable or less effective when mixed with one another. Further stoppers 14,14' may be included to permit the separation and subsequent sequential delivery of three or more substances. In one embodiment, a first substance may be delivered using the syringe assembly 10 and the delivery process may then be interrupted so that the needle 30 (or alternative applicator) may be changed prior to the delivery of the second substance using the same syringe assembly 10. Indeed, in the case where three or more substances are to be delivered, the needle 30 or other applicator may be changed prior to the delivery of each or any of the substances during the (interrupted) delivery procedure.

In another arrangement, the stopper 14 may be used to isolate a single volume of fluid from contact with certain components of the syringe assembly 10. In the example shown in FIG. 4A, the first volume 24 is defined between the stopper 14 and the plunger element 32 and contains a first fluid. The stopper 14 is disposed in the barrel 12 against the tapered forward portion 12b of the barrel 12 such that no further forward axial movement of the stopper 14 in the barrel 12 is possible. The second volume 26, axially forward of the stopper 14, does not contain any fluid or medicament. Thus, the first fluid is maintained in the first volume 24 and is isolated from the opening 12a of the barrel 12 and the needle 30. In some embodiments, it may be desirable to have some "take-up" such that the stopper 14 is initially disposed axially rearward of the tapered forward portion 12b of the barrel 12.

This arrangement may be advantageous in keeping sensitive medicaments isolated from the materials of the needle 30 and any adhesives used to affix the needle 30 to the opening 12a prior to actuation of the syringe assembly 10. Such contact between sensitive medicaments and the materials of the needle, any adhesives used to affix the needle in place, or any residual tungsten left from the manufacture of the syringe assembly (i.e. when forming the narrowed outlet 12a) may reduce or null the efficacy of the medicament over time. The arrangement shown in FIG. 4A therefore allows sensitive medicaments to be stably stored in a syringe assembly 10 without the risk of its efficacy being reduced through material contamination. In an isolated configuration (which may be achievable in any embodiment of the present invention), the medicament is only in contact with a limited number of materials, for example the stopper 14, the syringe barrel 12 and any silicon, if present (if, for example, the internal surface of the barrel 12 is siliconised). With limited contact between the materials of the syringe assembly 10 and the medicament, it is easier to determine extractables and leachables.

When the user is ready to deliver the first fluid in the first volume 24, the needle is inserted into the injection site and a force is applied to the plunger element 32 which in turn applies a force to the stopper 14 via the incompressible fluid in the first volume 24. If the stopper 14 is initially in the position shown in FIG. 4A against the tapered forward portion 12b, then the stopper is unable to move axially forwards and the pressure of the first fluid increases. If, however, there is some "take-up", and the stopper 14 is initially axially rearward of the tapered forward portion 12b, then the stopper 14 moves axially forwardly under the influence of the force applied to the plunger element 32 until it reaches the tapered forward portion 12b, at which point the pressure of the first fluid begins to increase. When the pressure of the first fluid exceeds the pressure threshold required to move the resilient seal 22 from the sealing configuration to the open configuration, the resilient seal 22 moves to the open configuration and the stopper permits the first fluid to leave the first volume 24 and enter the second volume 26 and be expelled from the syringe assemble 10 through the opening 12a and needle 30.

Figure 4A:
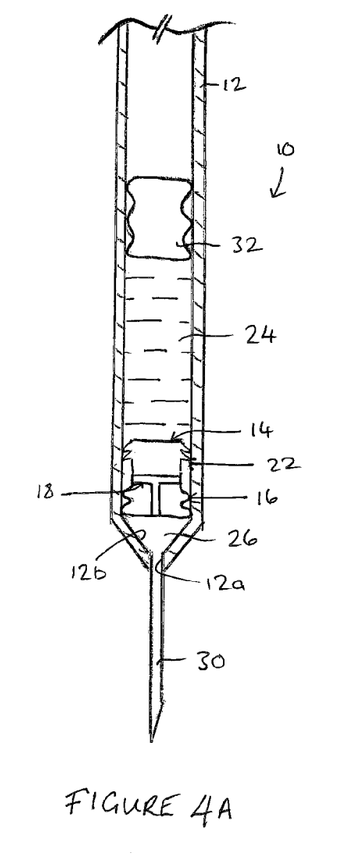
FIG. 4A is a partial cross sectional view of a syringe assembly in accordance with another embodiment of the present invention containing a single fluid prior to actuation.
Figure 4B:
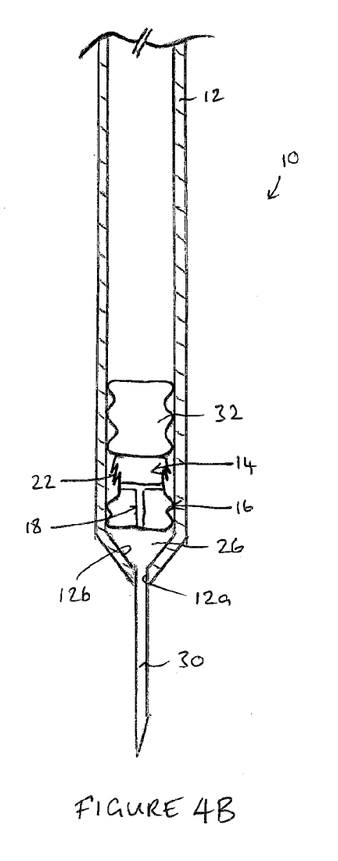
FIG. 4B is a partial cross sectional view of the syringe assembly of FIG. 4A after delivery.

Continued force on the plunger element 32 causes the plunger element 32 to continue to move axially forwardly towards the stationary stopper 14, decreasing the size of the first volume as it does so until the first volume 24 is reduced to substantially zero. At this point, delivery is complete and the user may remove the needle 30 from the injection site.

Since the stopper 14 is not required to move axially within the barrel 12, the stopper 14 may be fixed axially within the barrel 12. Examples of how the stopper 14 may be axially fixed within the barrel include but are not limited to radio frequency (RF) welding or heat welding. In other preferred embodiments, the stopper 14 may be retained axially within the barrel 12 simply by friction between the stopper 14 and the barrel 12. Alternatively or additionally, the stopper 14 may be prevented from moving axially forwardly in the barrel 12 by abutment with the tapered forward portion 12b of the barrel 12.

A further embodiment of the invention is shown in FIGS. 5A to 5D which depict the various stages of operation of a syringe assembly 10. In particular, the syringe assembly 10 of FIGS. 5A to 5D is for mixing two substances prior to delivery. For example, the two substances may include a dry or lyophilized medicament and a fluid diluent, or a dry or lyophilized medicament and a fluid medicament. It may be desirable for stability and/or efficacy reasons to keep the wet and dry substances separated prior to delivery (e.g. during storage of the syringe assembly 10).

Figure 5A:
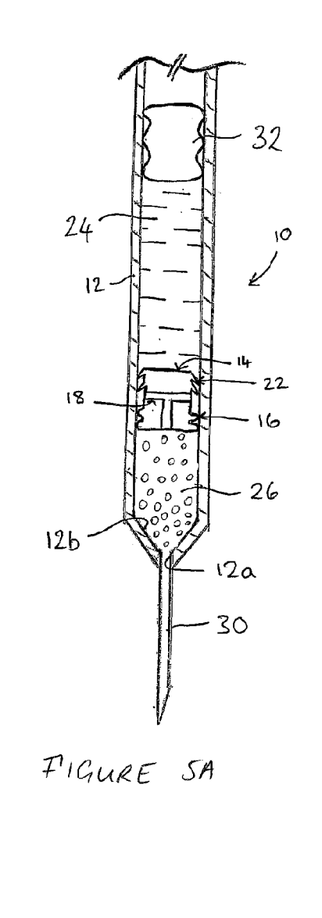
FIG. 5A is a partial cross sectional view of a mixing syringe assembly in accordance with an embodiment of the present invention prior to actuation.

The syringe assembly 10 of FIG. 5A is largely similar to that described above in relation to FIG. 3A. The first volume 24 contains a fluid while the second volume 26 contains a dry or lyophilized substance. The stopper 14 initially separates the first and second volumes 24,26 just as described above with reference to FIG. 3A. However, the stopper 14 of the syringe assembly 10 of FIG. 5A is configured in the barrel 12 such that the force at the fluid pressure threshold that determines when the resilient seal 22 moves from the sealing configuration to the open configuration is less than the force required to move the stopper 14 axially in the barrel 12 (i.e. that required to overcome friction and other axial resistive forces).

Figure 5B:
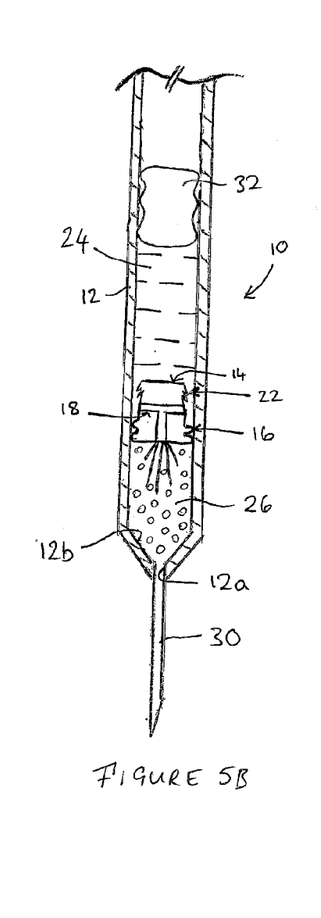
FIG. 5B is a partial cross sectional view of the mixing syringe assembly of FIG. 5A during mixing.

Therefore, when the syringe assembly is actuated by applying a forwardly axial force on the plunger element 32, the increase in fluid pressure in the first volume 24 causes the resilient seal 22 to move from the sealing configuration to the open configuration whilst the stopper 14 remains axially stationary in the barrel 12. FIG. 5B shows the syringe assembly of FIG. 5A during the "mixing" stage, where the resilient seal 22 is in its open configuration and the axially forwardly advancing plunger element 32 is pressurizing the fluid in the first volume and causing it to flow into the second volume via the channel 18, while the stopper 14 remains axially stationary within the barrel 12. The fluid from the first volume 24 therefore mixes with the dry or lyophilized substance in the second volume 26 to form a solution or mixture. In some embodiments, the stopper 14 may additionally comprise a nozzle or spray head (not shown) at or near the first opening 20a to facilitate mixing of the fluid and dry or lyophilized substance in the second volume 26.

Figure 5C:
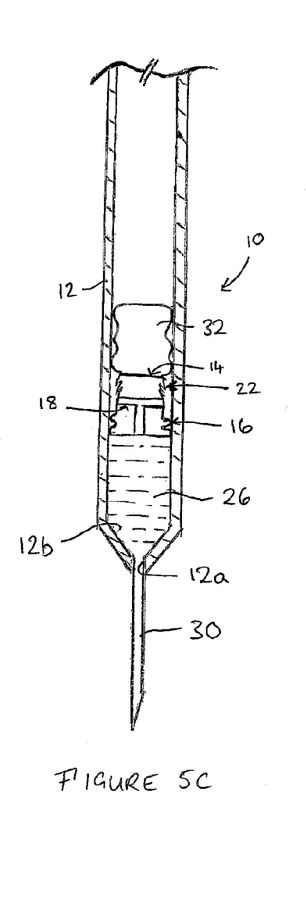
FIG. 5C is a partial cross sectional view of the mixing syringe assembly of FIGS. 5A and 5B at the start of delivery.

Continued axially forward movement of the plunger element 32 results in the plunger element 32 reaching the stopper 14 and reducing the first volume 24 to zero. At this point, substantially all of the fluid from the first volume 24 has flowed through the channel 18 and into the second volume 26 to form a solution or mixture. Once the plunger element 32 has met the stopper 14, as shown in FIG. 5C, further axially forwardly movement of the plunger element 32 causes the stopper 14 to move axially forwardly in the barrel as the forward force applied to the stopper 14 exceeds the axially rearwardly acting frictional and resistive forces that resist forward axial movement of the stopper 14 in the barrel 12.

Figure 5D:
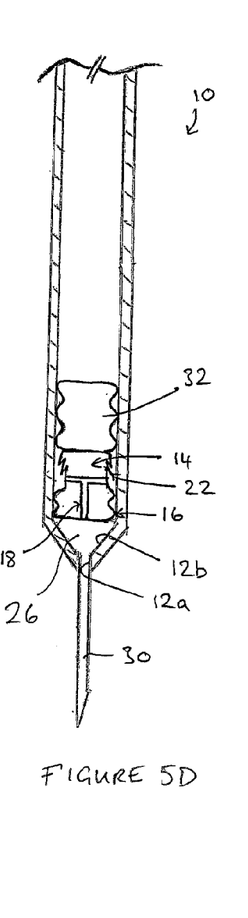
FIG. 5D is a partial cross sectional view of the mixing syringe assembly of FIGS. 5A to 5C after delivery.

Axially forwardly movement of the stopper 14 in the barrel 12 causes the solution or mixture contained in the second volume 26 to be expelled through the opening 12a of the barrel through the needle 30 and into the injection site that the needle is staked into. FIG. 5D shows the syringe assembly 10 at the end of delivery where the plunger element 32 and stopper 14 have moved to their forwardmost axial position in the barrel 12, with the stopper 14 abutting the tapered forward portion 12b of the barrel 12. At this point, the syringe assembly 10 may be removed from the injection site.

An alternative embodiment of a mixing-type syringe assembly 10 in accordance with the present invention is shown in FIGS. 6A to 6D. In this embodiment, the stopper 14" includes a friction clamp 34 that increases the frictional forces required to move the stopper 14" axially forwardly within the barrel 12. In one embodiment, the stopper 14" may be a two-shot moulding where the first shot forms the friction clamp 34 from a plastics material or the like and the second shot forms the remainder of the stopper 14" from an elastomer material or the like. The stopper 14" additionally has a socket 36 formed therein that is capable of receiving a complementary key 32a that is formed on the front side of the plunger element 32. When the key 32a is received in the socket 36, the clamping load (i.e. the frictional and resistive forces) provided by the friction clamp 34 is reduced, thereby lowering the threshold force required to move the stopper 14" axially forwardly in the barrel 12.

Figure 6A:
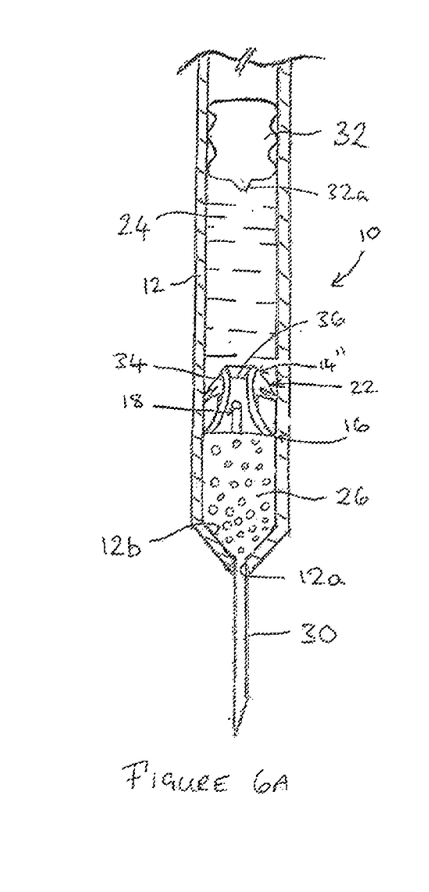
FIG. 6A is a partial cross sectional view of a mixing syringe assembly in accordance with an alternative embodiment of the present invention prior to actuation.
Figure 6B:
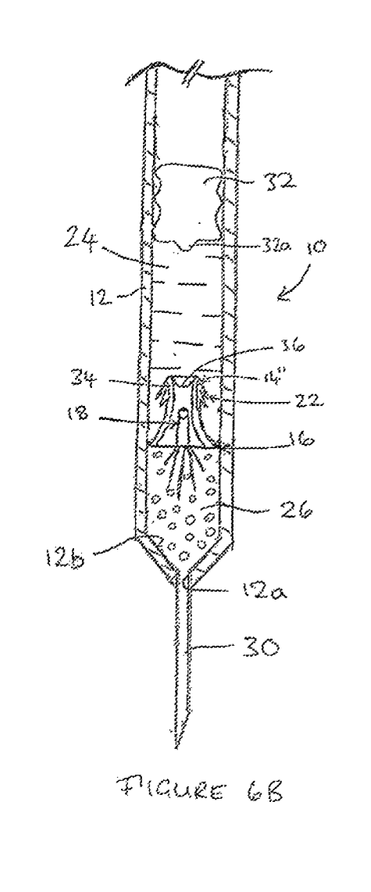
FIG. 6B is a partial cross sectional view of the mixing syringe assembly of FIG. 6A during mixing.

The arrangement shown in FIG. 6A is equivalent to that shown in FIG. 5A where a fluid substance is contained in the first volume 24 and a dry or lyophilized substance is contained in the second volume 26, prior to actuation. Similarly, FIG. 6B shows an equivalent arrangement to that shown in FIG. 5B, where the axially forwardly force on the plunger element 32 has caused the plunger element 32 to move axially forwardly in the barrel 12 towards the stationary stopper 14" causing the resilient seal to move into the open configuration and forcing the fluid from the first volume 24 to flow into the second volume 26 through the channel 18.

Figure 6C:
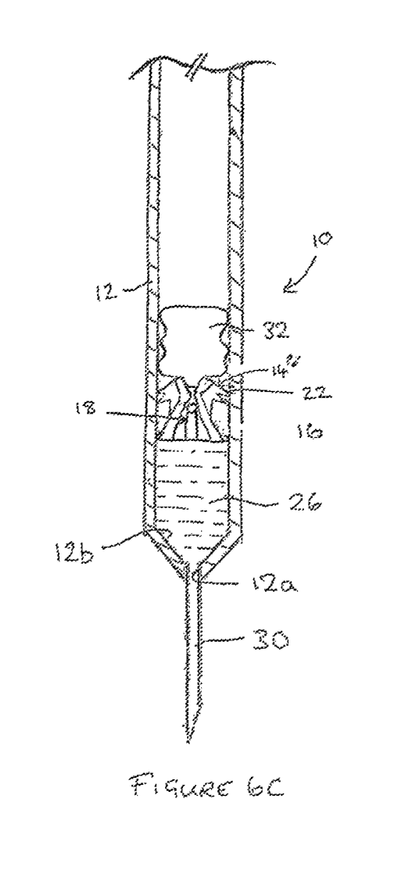
FIG. 6C is a partial cross sectional view of the mixing syringe assembly of FIGS. 6A and 6B at the start of delivery.
Figure 6D:
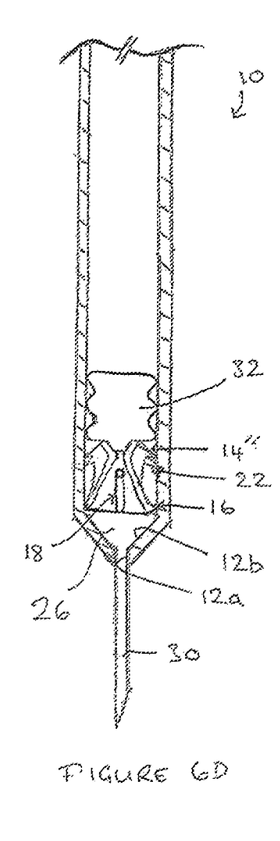
FIG. 6D is a partial cross sectional view of the mixing syringe assembly of FIGS. 6A to 6C after delivery.

In the arrangement shown in FIG. 6C, the plunger element 32 has moved axially forwardly in the barrel 12 and has met the stopper 14" such that the key 32a of the plunger element 32 is inserted into the socket 36 of the stopper 14". As described above, the mating of the key 32a and socket 36 components causes the clamping load of the stopper 14" to be reduced. Therefore, further axially forward movement of the plunger element 32 causes axially forward movement of the stopper 14", thus expelling the solution or mixture formed in the second volume 26 from the syringe assembly 10 via the opening 12a and needle 30. FIG. 6D shows the syringe assembly 10 at the end of delivery where the plunger element 32 and stopper 14" have moved to their forwardmost axial position in the barrel 12, with the stopper 14" abutting the tapered forward portion 12b of the barrel 12. At this point, the syringe assembly 10 may be removed from the injection site.

The arrangement of FIGS. 6A to 6D has the additional advantage over the arrangement of FIGS. 5A to 5D in that the force required to move the stopper 14" is higher due to the presence of the friction clamp 34. However, the key 32a and socket 36 arrangement of the embodiment of FIGS. 6A to 6D means that the force required to actually move the stopper 14" axially forwardly when desired is achievable within the reasonable operating limits of the syringe assembly 10. Therefore, the friction clamp 34 provides less risk of unwanted axial movement of the stopper 14" prior to the completion of mixing between the first volume 24 and the second volume 26.

The syringe assembly 10 of the present invention may be used as a manual device or as part of an autoinjector device. In particular, the syringe assembly 10 may be configured such that the needle 30 is automatically inserted and removed from the injection site, prior to and after delivery, respectively.

Either of the described stoppers 14,14' and any described alternatives or modifications of the stoppers 14,14' may be utilized in a syringe assembly 10 in accordance with the present invention. Additionally, the stopper 14" described in relation to FIGS. 6A to 6D may be used in "mixing"-type devices within the scope of the present invention. All stoppers in accordance with the present invention are particularly advantageous as each provides an effective and reliable two-way valve for separating two substances or isolating a single substance. The stopper may be used in existing syringes thereby negating the requirement for bespoke syringes. Additionally, the stopper of the present invention may be easily and cost-effectively moulded in comparison to prior art components that seek to provide a similar effect. Thus the syringe assembly 10 of the present invention is easy to manufacture in comparison to more complicated prior art arrangements. A further advantage of the syringe assembly 10 of the present invention is that it may be filled with relative ease in comparison with prior art devices. Each substance is introduced into the barrel sequentially from the rear (i.e. the end opposite the narrowed opening or outlet) with the stopper (or stoppers) being inserted in the sequence where desired. Therefore, standard syringe filling apparatus that is common in the art may be used to fill the syringe assembly, and no specially adapted filling apparatus need necessarily be used.

Two or more stoppers 14,14' may be employed in a single syringe assembly 10 to provide selective sealing between several volumes in the syringe assembly 10. For example, three medicaments may be delivered sequentially by utilizing two stoppers 14,14' intermediate the opening 12a and the plunger element 32 or equivalent means for providing a forward force. Indeed, the syringe assembly 10 may consist of a combination of the embodiments shown in FIGS. 3A to 3C and FIGS. 4A to 4B in that a front stopper 14,14' may be used to isolate the contents of the syringe assembly 10 from the opening 12a and needle 30 whilst further stoppers 14,14' may be utilized to permit a multi-dose, sequential delivery. Additionally or alternatively, the syringe assembly 10 may be a combination of any of the described embodiments so that the syringe assembly 10 is capable of any one or more of: sequential delivery, mixing of two or more substances, and medicament isolation. Indeed, the syringe assembly 10 may be arranged to be capable of all three of these modes of operation, such that medicaments are initially isolated from one another and the narrowed outlet (and any needle present). Upon actuation of the syringe assembly 10, two or more of the substances may be mixed in accordance with the mechanism described above in relation to FIGS. 5A to 5D or FIGS. 6A to 6D and then delivered, before being delivered, following the sequential delivery of one or more substances stored axially rearward of the two or more substances that are mixed.

Instead of an integral narrowed opening 12a, the syringe assembly 10 may include a separate component that serves as a narrowed opening 12a for allowing the expulsion of fluid from the syringe assembly 10.

The syringe assembly 10 of the present invention may be used with a needle 30 or other applicator in fluid communication with the opening 12a.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A syringe assembly comprising:
   a barrel for containing one or more medicaments, a narrowed outlet for allowing the expulsion of said one or more medicaments from said barrel through said outlet; and
   a stopper disposed in the barrel defining and separating a first volume and a second volume within the syringe assembly, the stopper comprising:
      a permanent seal fluidly sealing the stopper to the barrel along an entire perimeter of the stopper intermediate the first volume and the second volume; and
      a channel bypassing the permanent seal, the channel having a first opening in fluid communication with the second volume and a second opening selectively sealed from the first volume by a resilient seal;
   where the resilient seal is moveable between a sealing configuration and an open configuration to selectively seal the channel from the first volume, where in the sealing configuration the resilient seal fluidly seals against the barrel to fluidly seal the stopper to the barrel so as to fluidly isolate said second opening of the channel from the first volume, and in the open configuration the second opening of the channel is in fluid communication with the first volume; and
   wherein the resilient seal is moveable from the sealing configuration to the open configuration upon fluid pressure in the first volume or the second volume exceeding a first pressure threshold.

2. The syringe assembly according to claim 1, wherein the stopper is axially moveable within the barrel upon application of an axial force on the stopper.

3. The syringe assembly according to claim 2, wherein the axial force required to move the stopper within the barrel is less than a force provided by a fluid at the first pressure threshold.

4. The syringe assembly according to claim 3, wherein said first volume contains a fluidic substance and said second volume contains a dry or lyophilized substance.

5. The syringe assembly according to claim 2, wherein the axial force required to move the stopper within the barrel is greater than the force provided by a fluid at the first pressure threshold.

6. The syringe assembly according to claim 5, wherein the stopper further comprises a friction clamp that is moveable between a clamping position and a non-clamping position, where a higher force is required to axially move the stopper in the barrel when the friction clamp is in the clamping position than when the friction clamp is in the non-clamping position.

7. The syringe assembly according to claim 6, further comprising a moveable plunger element disposed in the barrel for pressurising a fluid in the first volume, where the stopper is disposed in the barrel intermediate the plunger element and the narrowed outlet of the barrel, wherein the plunger element comprises a key and the stopper comprises a socket complementary to said key, and wherein engagement of the key in the socket moves said friction clamp to said non-clamping position.

8. The syringe assembly according to claim 1, wherein the resilient seal comprises one or more flexible elements.

9. The syringe assembly according to claim 8, wherein said one or more flexible elements partly extends circumferentially around said stopper and the remainder of the stopper forms a seal with the barrel circumferentially around said one or more flexible elements.

10. The syringe assembly according to claim 8, wherein said one or more flexible elements extends entirely circumferentially around said stopper.

11. The syringe assembly according to claim 8, wherein the resilient seal comprises at least two flexible elements.

12. The syringe assembly according to claim 11, wherein the at least two flexible elements are axially aligned with one another.

13. The syringe assembly according to claim 8, wherein the channel comprises at least one axial channel part and at least one additional channel part arranged substantially perpendicularly to said at least one axial channel and in fluid communication therewith.

14. The syringe assembly according to claim 13, wherein the permanent seal comprises at least one flange projecting outwardly from said stopper along the entire perimeter of the stopper.

15. The syringe assembly according to claim 14, wherein the permanent seal comprises at least two flanges projecting outwardly from said stopper along the entire perimeter of the stopper, wherein the at least two flanges are arranged in axial alignment with one another.

16. The syringe assembly according to claim 1, further comprising a pressure source for pressurising a fluid in the barrel.

17. The syringe assembly according to claim 16, wherein said pressure source comprises an axially moveable plunger element disposed in the barrel, where the stopper is disposed in the barrel intermediate the plunger element and the narrowed outlet of the barrel.

18. The syringe assembly according to claim 17, wherein said plunger element comprises a plunger stopper and a plunger rod connected to the plunger stopper for axially moving the plunger stopper in the barrel.

19. The syringe assembly according to claim 1, wherein one or both of said first volume and said second volume is a medicament volume for containing said one or more medicaments.

20. The syringe assembly according to claim 1, further comprising a needle in fluid communication with the narrowed outlet of said barrel, wherein said barrel and the narrowed outlet are integrally formed and said barrel tapers towards the narrowed outlet.

21. The syringe assembly according claim 1, wherein said stopper is a first stopper, and the syringe assembly further comprises one or more additional stoppers each comprising the features of the first stopper, wherein the one or more additional stoppers separate and define further volumes within the syringe assembly axially rearward of the first stopper.

22. An autoinjector comprising the syringe assembly according to claim 1.

23. A syringe assembly comprising:
    a barrel for containing one or more medicaments, a narrowed outlet for allowing the expulsion of said one or more medicaments from said barrel through said outlet; and a stopper disposed in the barrel defining and separating a first volume and a second volume within the syringe assembly, the stopper comprising:
- a permanent seal fluidly sealing the stopper to the barrel along an entire perimeter of the stopper intermediate the first volume and the second volume; and
- a channel bypassing the permanent seal, the channel having a first opening in fluid communication with the second volume and a second opening selectively sealed from the first volume by a resilient seal;

where the resilient seal is moveable between a sealing configuration and an open configuration to selectively seal the channel from the first volume, where in the sealing configuration the resilient seal fluidly seals the stopper to the barrel so as to fluidly isolate said second opening of the channel from the first volume, and in the open configuration the second opening of the channel is in fluid communication with the first volume;

wherein the resilient seal is moveable from the sealing configuration to the open configuration upon fluid pressure in the first volume or the second volume exceeding a first pressure threshold;

wherein the stopper is axially moveable within the barrel upon application of an axial force on the stopper;

wherein the axial force required to move the stopper within the barrel is less than a force provided by a fluid at the first pressure threshold; and wherein the stopper further comprises a nozzle or spray head at the first opening of the stopper.

24. A method of using a syringe assembly comprising the steps of:
i) providing the syringe assembly, wherein the syringe assembly includes a barrel for containing one or more medicaments, a narrowed outlet for allowing the expulsion of said one or more medicaments from said barrel through said outlet; and
a stopper disposed in the barrel defining and separating a first volume and a second volume within the syringe assembly, the stopper comprising:
- a permanent seal fluidly sealing the stopper to the barrel along an entire perimeter of the stopper intermediate the first volume and the second volume; and
- a channel bypassing the permanent seal, the channel having a first opening in fluid communication with the second volume and a second opening selectively sealed from the first volume by a resilient seal;
where the resilient seal is moveable between a sealing configuration and an open configuration to selectively seal the channel from the first volume, where in the sealing configuration the resilient seal fluidly seals against the barrel to fluidly seal the stopper to the barrel so as to fluidly isolate said second opening of the channel from the first volume, and in the open configuration the second opening of the channel is in fluid communication with the first volume; and wherein the resilient seal is moveable from the sealing configuration to the open configuration upon fluid pressure in the first volume or the second volume exceeding a first pressure threshold and containing a first fluid in the first volume; and
ii) applying a force to pressurise the fluid so that the resilient seal moves to the open configuration and permits the expulsion of the fluid through the narrowed outlet via the channel of the stopper.

25. The method of using the syringe assembly of claim 24 further comprising the steps of:
i) providing the syringe assembly containing the first fluid in the first volume and a second fluid in the second volume;
ii) applying a force to pressurise the first fluid to move the stopper axially forwardly within the barrel to expel the second fluid through the narrowed outlet;
iii) allowing the stopper to travel axially forwardly in the barrel to its forwardmost position; and
iv) continuing to apply a force to pressurize the first fluid so that the resilient seal moves to the open configuration and permits the expulsion of the first fluid through the narrowed outlet via the channel of the stopper.

26. The method according to claim 25, wherein the syringe assembly provided in step i) further comprises a first applicator in fluid communication with the narrowed outlet, and wherein subsequent to performing step ii) and prior to performing step iv) the first applicator is replaced with a second applicator.

27. The method according to claim 26, wherein one or both of the first applicator and second applicator is a needle.

28. A method of using a syringe assembly comprising the steps of:
i) providing the syringe assembly, wherein the syringe assembly includes a barrel for containing one or more medicaments, a narrowed outlet for allowing the expulsion of said one or more medicaments from said barrel through said outlet; and a stopper disposed in the barrel defining and separating a first volume and a second volume within the syringe assembly, the stopper comprising:
- a permanent seal fluidly sealing the stopper to the barrel along an entire perimeter of the stopper intermediate the first volume and the second volume; and
- a channel bypassing the permanent seal, the channel having a first opening in fluid communication with the second volume and a second opening selectively sealed from the first volume by a resilient seal; where the resilient seal is moveable between a sealing configuration and an open configuration to selectively seal the channel from the first volume, where in the sealing configuration the resilient seal fluidly seals against the barrel to fluidly seal the stopper to the barrel so as to fluidly isolate said second opening of the channel from the first volume, and in the open configuration the second opening of the channel is in fluid communication with the first volume; and wherein the resilient seal is moveable from the sealing configuration to the open configuration upon fluid pressure in the first volume or the second volume exceeding a first pressure threshold and containing a fluidic substance in the first volume and a dry or lyophilized substance in the second volume;
ii) applying a force to pressurise the fluidic substance so that the resilient seal moves to the open configuration and permits the flow of the fluidic substance from the first volume to the second volume via the channel to form a solution or mixture in the second volume; and
iii) applying a force to the stopper to move the stopper axially forwardly so as to expel the solution or mixture from the second volume through the narrowed outlet.

29. The method according to claim 28, wherein the applied forces are provided by moving a plunger element axially forwardly in the barrel, wherein the stopper is disposed intermediate the plunger element and the narrowed outlet, and wherein the force applied to the stopper in step iii) occurs when the plunger element contacts the stopper following the expulsion of substantially all of the fluidic substance from the first volume.

30. The method according to claim 29, wherein the stopper further comprises a friction clamp that is moveable between a clamping position and a non-clamping position, where a higher force is required to axially move the stopper in the barrel when the friction clamp is in the clamping position than when the friction clamp is in the non-clamping position, wherein the plunger element comprises a key and the stopper comprises a socket complementary to said key, and wherein engagement of the key in the socket moves said friction clamp to said non-clamping position.

* * * * *